United States Patent
Mandimutsira et al.

(10) Patent No.: US 8,779,211 B2
(45) Date of Patent: Jul. 15, 2014

(54) RATE AND SELECTIVITY IMPROVEMENT IN HYDROFORMYLATION OF ALLYL ALCOHOL

(71) Applicant: Lyondell Chemical Technology, L.P., Houston, TX (US)

(72) Inventors: Beaven S. Mandimutsira, Wynnewood, PA (US); Daniel F. White, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 13/904,697

(22) Filed: May 29, 2013

(65) Prior Publication Data

US 2014/0005440 A1    Jan. 2, 2014

Related U.S. Application Data

(60) Provisional application No. 61/652,648, filed on May 29, 2012.

(51) Int. Cl.
*C07C 45/50*    (2006.01)

(52) U.S. Cl.
USPC .......................................................... 568/454

(58) Field of Classification Search
USPC .......................................................... 568/454
See application file for complete search history.

(56) References Cited

U.S. PATENT DOCUMENTS

| | | |
|---|---|---|
| 6,127,584 A | 10/2000 | Zajacek et al. |
| 6,426,437 B1 | 7/2002 | Shum et al. |
| 7,655,821 B1 | 2/2010 | White et al. |
| 7,790,932 B1 | 9/2010 | White et al. |

FOREIGN PATENT DOCUMENTS

| | | |
|---|---|---|
| JP | 06-279344 A | 10/1994 |
| JP | 06-279345 A | 10/1994 |

OTHER PUBLICATIONS

PCT/US2013/043122 International Search Report and Written Opinion mailed Sep. 23, 2013.

*Primary Examiner* — Sikarl Witherspoon

(57) ABSTRACT

A process for producing 4-hydroxybutyraldehyde comprises reacting allyl alcohol with $CO/H_2$ in a reactor in the presence of a catalyst system comprising rhodium complex and trans-1,2-bis[bis(3,5-di-n-alkylphenyl)phosphino]-cyclobutane at a pressure of about 50 psi or lower.

13 Claims, 4 Drawing Sheets

Results summary showing superiority of the Rh-Ligand B2 over the Rh-Ligand A1 catalyst system in the hydroformylation of allyl alcohol under low pressure conditions

| Catalyst system | [CO]liq | [H$_2$]liq | Rh (ppm) | C$_3$ Sel | BDO Sel | MPDiol Sel | l:b | Rate (k) hr$^{-1}$ | BDOe Yield | Δ BDOe | Δ C$_3$ | Δ BDO | Δ MPDiol |
|---|---|---|---|---|---|---|---|---|---|---|---|---|---|
| Ligand A1 | | | | | | | | | | | | | |
| C1 | 10.24 | 12.02 | 182 | 0.61% | 86.50% | 12.13% | 7.13 | 1.30 | 98.63% | | | | |
| C2 | 8.11 | 12.00 | 188 | 0.63% | 86.18% | 12.22% | 7.05 | 1.51 | 98.41% | | | | |
| C4 | 10.33 | 10.77 | 189 | 0.77% | 86.60% | 12.05% | 7.19 | 0.99 | 98.65% | | | | |
| C5 | 10.33 | 9.00 | 182 | 0.77% | 86.4% | 12.2% | 7.07 | 0.93 | 98.61% | | | | |
| Ligand B2 | | | | | | | | | | | | | |
| C1 | 10.36 | 11.99 | 197 | 0.52% | 88.86% | 10.18% | 8.72 | 1.75 | 99.04% | 0.42% | -0.09% | 19.48% | -18.26% |
| C2 | 8.19 | 11.96 | 189 | 0.60% | 88.64% | 10.26% | 8.64 | 2.12 | 98.90% | 0.49% | -0.03% | 20.10% | -18.41% |
| C4 | 10.34 | 10.72 | 186 | 0.48% | 88.85% | 10.32% | 8.61 | 1.53 | 99.17% | 0.52% | -0.28% | 18.68% | -16.51% |
| C5 | 10.30 | 8.82 | 206 | 0.46% | 88.74% | 10.39% | 8.54 | 1.30 | 99.13% | 0.52% | -0.31% | 19.21% | -17.18% |

Observed changes Ligand A1 to B2
- Rate increases
- BDOe increases ~0.5%
- BDO selectivity increases 18-20%
- MPDiol selectivity decreases 16-18% at constant BDO
- C$_3$ selectivity decreases (goes to MPDiol, i.e. MPDiol made at the expense of C$_3$)

*FIG. 1*

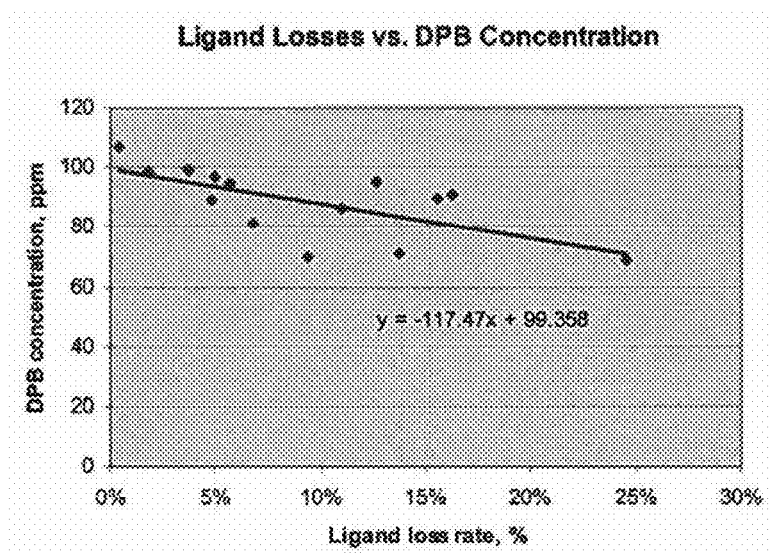

FIG. 2

Verification of rate increase from the Rh-Ligand A1 to Rh-Ligand B2 catalyst system in the low pressure hydroformylation of AA with two different Ligand B2 products

| Ligand/ Condition | [CO]liq | [H₂]liq | [Rh] (ppm) | AA brk-th R 601 | AA conv (%) | C₃ Sel | BDO Sel | MPDiol Sel | l:b | Rate (k) hr⁻¹ | Δ BDO | Δ MPDiol |
|---|---|---|---|---|---|---|---|---|---|---|---|---|
| Ligand A1: Condition 1 | 10.24 | 12.02 | 182 | 4.47 | 74.15 | 0.61% | 86.50% | 12.13% | 7.13 | 1.39 | | |
| Run 1 | | | | | | | | | | | | |
| Ligand B2: C1 | 10.31 | 12.00 | 185 | 3.81 | 78.14 | 0.58% | 88.68% | 10.08% | 8.79 | 1.62 | 17.97% | -18.80% |
| Run 2 | | | | | | | | | | | | |
| Ligand B2: C1 | 10.36 | 11.99 | 197 | 3.62 | 79.36 | 0.52% | 88.86% | 10.18% | 8.72 | 1.75 | 19.46% | -18.26% |

*Run2 has a higher rate due to the higher [Rh], 197 compared to 185 ppm in Run1

FIG. 3

RATE AND SELECTIVITY IMPROVEMENT IN HYDROFORMYLATION OF ALLYL ALCOHOL

CROSS-REFERENCE TO RELATED APPLICATIONS

This application claims benefit and priority of U.S. Provisional Patent Application No. 61/652,648 filed on May 29, 2012, which is incorporated herein by reference in its entirety.

STATEMENT REGARDING FEDERALLY SPONSORED RESEARCH OR DEVELOPMENT

Not applicable.

BACKGROUND

This section of this document introduces information about and/or from the art that may provide context for or be related to the subject matter described herein and/or claimed below. It provides background information to facilitate a better understanding of various aspects of the present invention. This is a discussion of "related" art. That such art is related in no way implies that it is also "prior" art. The related art may or may not be prior art. The discussion in this section of this document is to be read in this light, and not as admissions of prior art.

Diphenylphosphinobutane ("DPB") is a flexible diphosphine ligand with a bite angle of 97°. DIOP, 2,3-O-isopropylidene-2,3-dihydroxy-1,4-bis[bis(3,5-di-n-alkylphenyl)phosphino]butane ("Ligand A1") and trans-1,2-bis[bis(3,5-di-n-alkylphenyl)phosphino]-cyclobutane ("Ligand B2") are constrained diphosphine ligands with bite angles of between 100°-110°. DIOP, Ligand A1 and Ligand B2 have four carbons between the two phosphine moieties and will form a seven membered ring when coordinated to Rhodium ("Rh"). Such a catalyst system with Ligand A1 is disclosed and claimed in U.S. Pat. No. 7,271,295, incorporated by reference below. A catalyst system employing Ligand B2 is disclosed and claimed in U.S. Pat. No. 7,294,602, also incorporated by reference below.

The process of producing 4-hydroxybutyraldehyde ("HBA") comprises reacting allyl alcohol ("AA") with a $CO/H_2$ mixture in the presence of a catalyst, typically a Rh complex with phosphine ligands. The initial products are HBA and lesser value products such as 3-hydroxy-2-methylpionaldehyde ("HMPA") and byproducts such as n-propanol, ("n-Pr") and propionaldehyde, ("PA"). The hydroxyl aldehydes are hydrogenated to give the final corresponding diols, Butanediol ("BDO") and 2-Methylpropane diol ("MPDiol").

While catalyst systems can employ both mono- and bidentate phosphine ligands, the latter have been the focus of research because they have shown marked improvements in the yield to HBA over HMPA coupled with the reduction of process losses to the byproducts n-Pr and PA. Progression in improvements from the catalyst system consisting of the monodentate, triphenylphosphine, ("TPP") as the main ligand to systems containing, bidentate phosphines such as DIOP and 2,3-O-isopropylidene-2,3-dihydroxy-1,4-bis[bis(3,5-di-n-alkylphenyl)phosphino]butane, (Ligand A1), U.S. Pat. No. 7,271,295 have been achieved. One ligand in these series, trans-1,2-bis[bis(3,5-di-n-alkylphenyl)phosphino]-cyclobutane, ("Ligand B2"), as disclosed in U.S. Pat. No. 7,294,602, has been shown on batch scale to give improved results, 20% reduction in MPDiol in favor of BDO, compared to Ligand A1 while maintaining low n-Pr make and preserving rate. This disclosure serves to reveal more advantages of the Ligand B2 system observed under continuous pilot run conditions.

Several hydroformylation processes for diphosphines are available to the art, all of which are competent for their intended purposes. The art however is always receptive to improvements or alternative means, methods and configurations. Therefore the art will well receive the technique described herein.

SUMMARY

A process for producing HBA comprises reacting AA with $CO/H_2$ in a reactor in the presence of a catalyst system comprising a rhodium complex and Ligand A1 or Ligand B2 at a pressure of about 50 psi or lower.

The above paragraph presents a simplified summary of the presently disclosed subject matter in order to provide a basic understanding of some aspects thereof The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The invention may be understood by reference to the following description taken in conjunction with the accompanying drawings, in which like reference numerals identify like elements, and in which:

FIG. 1 is a table summarizing the superiority of the Rh-Ligand B2 over the Rh-Ligand A1 system in the hydroformylation of AA under low pressure conditions.

FIG. 2 shows the impact that DPB concentration has on ligand loss rate using a Ligand A1 catalyst. For example, at approximately 100 ppm DPB concentration, the ligand loss rate is slightly over 0%; at approximately 80 ppm DPB, the ligand loss rate is 17.5%. One "best fit" curve fitting method equates the DPB concentration in ppm to $(-117.47 \times$ the ligand loss rate (%))+99.358.

FIG. 3 is a table comparing AA hydroformylation with two different Ligand B2 products under low pressure hydroformylation conditions and show rate increase is an intrinsic property of Ligand B2 and not source specific.

Figure 4:
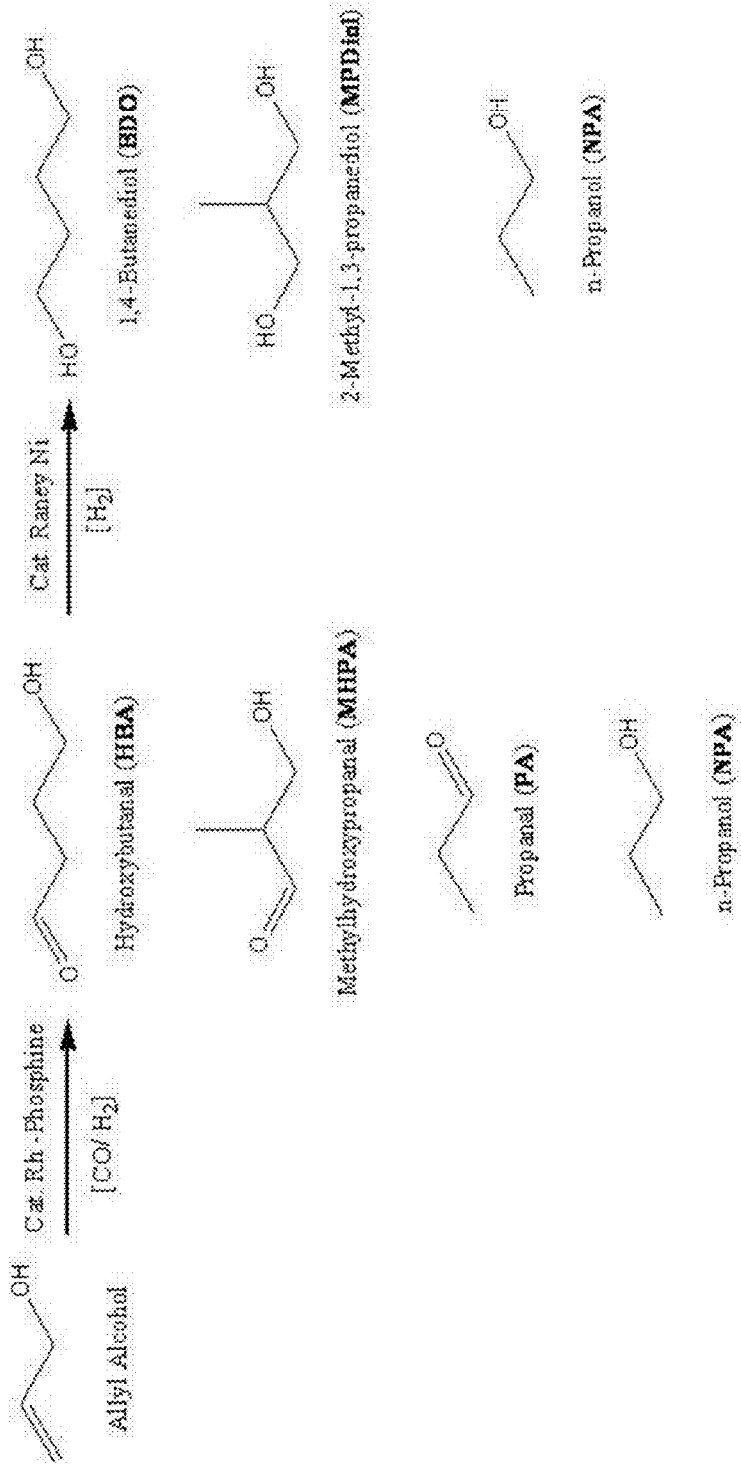
FIG. 4 graphically illustrates AA to BDO chemistry.
Figure 5:
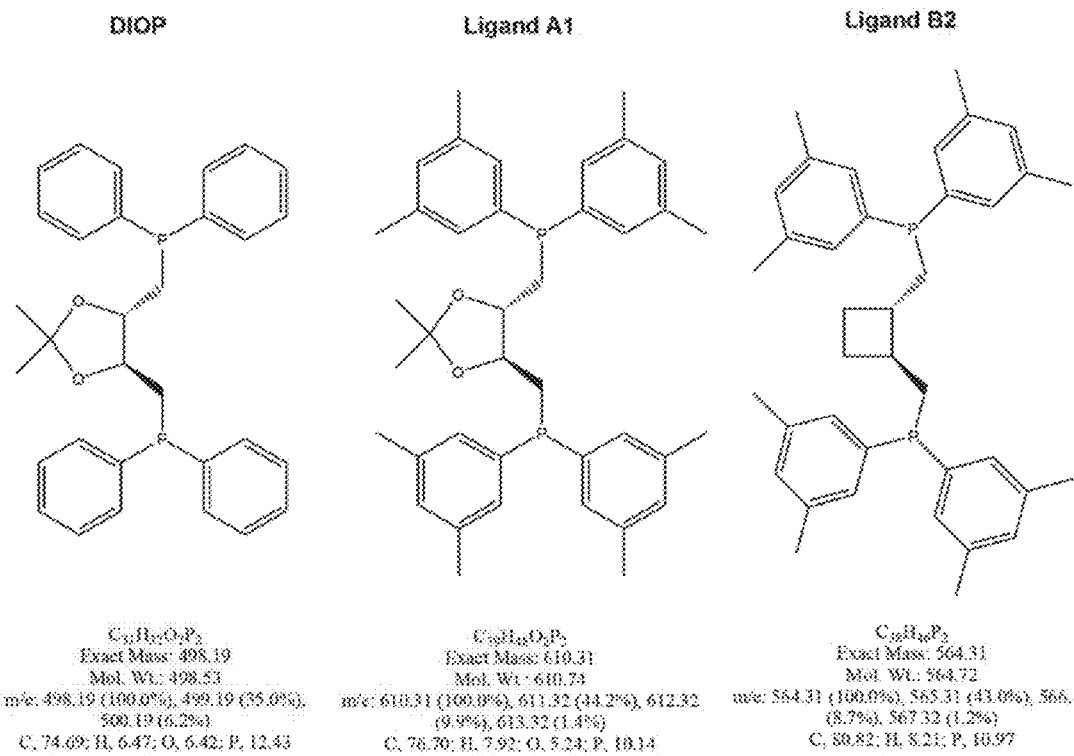
FIG. 5 graphically illustrates and provides information regarding the Ligands A1 and B2 and DIOP.
Figure 6:
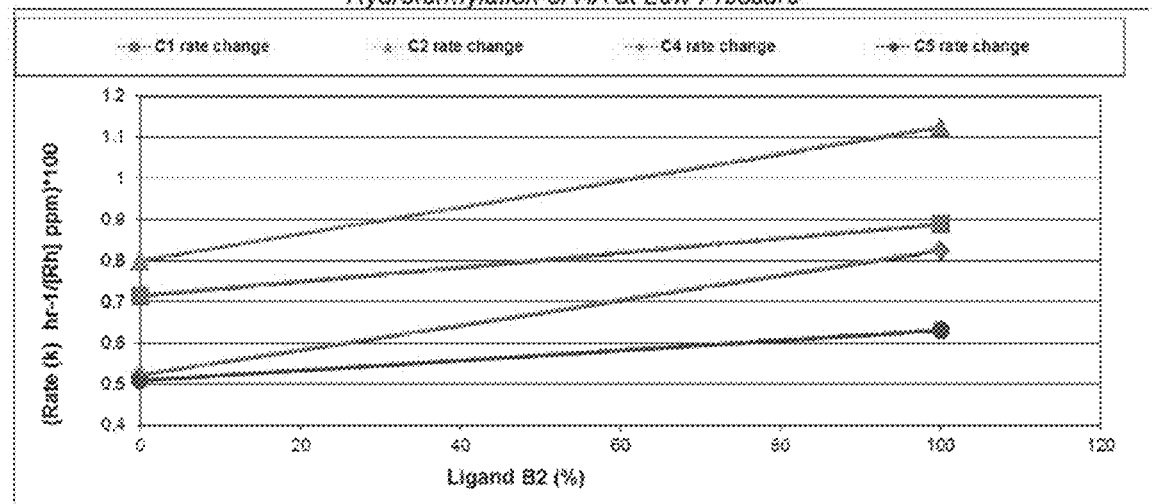
FIG. 6 graphs the rate differences between Rh-Ligand A1 and Rh-Ligand B2 catalysts under low pressure hydroformylation conditions.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

We have discovered that hydroformylation of AA under low pressure conditions, with the Rh-Ligand B2 system results in both an increase in rate and total diols, (Butanediol equivalents, or "BDOe") yield and a decrease in n-Pr make compared to the Rh-Ligand A1 system. The typical low pressure conditions explored were as follows, (50 psig, 145° F. with AA feed concentration of 17%, (feed rate=140 cc/hr); [Rh], 180-200 ppm; (Ligand B2:Rh=1.5); [CO]liq, 8-10.3 mg-mol/L, (70-100 SLH) and [$H_2$]liq 8-12 mg-mol/L, (150-200 SLH)). The results are summarized in the table of FIG. 1 and they show that under all the tested conditions going from Ligand A1 to Ligand B2: the rate of reaction increases; BDOe yield increases 0.5%, with BDO selectivity increasing ~20% (with respect to MPDiol) while MPDiol selectivity decreases ~18%. In all conditions tested the n-Pr selectivity decreased.

Due to the observed increase in rate of reaction and BDOe yield, one potential benefit is that the use of Ligand B2 at low pressure conditions would provide an opportunity for running the hydroformylation process at lower temperature or at lower [Rh] while maintaining yield.

Results summary showing the superiority of the Rh-Ligand B2 over the Rh-Ligand A1 system in the hydroformylation of AA under low pressure conditions are shown in the table of FIG. 1.

Thus, the presently disclosed technique is a process for producing HBA comprising reacting AA with CO/$H_2$ in a reactor in the presence of a catalyst system comprising rhodium complex and Ligand B2 at a pressure of about 50 psi or lower. As used herein, the term "low pressure" may be considered to be less than about 50 psi, wherein the term "about" represents margin of error introduced in the operations of any process such as that described herein. Furthermore, it is believed that the unexpected results documented above will result in such a process in at least the range of 50 psi to about 35 psi.

In some variations of this process, the process may have a BDO selectivity greater than 86.6% and preferably greater than 88.64%, a MPDiol selectivity lower than 12.05% and preferably lower than 10.39%, a BDO selectivity: MPDiol selectivity ratio greater than 7.19 and preferably greater than 8.54, or some combination of these features.

In other variations on this process, the process may further have a BDOe yield greater than 98.65% and preferably greater than 98.90% or a BDOe yield at least 0.42% higher than a process utilizing Ligand A1 catalyst instead of Ligand B2 catalyst, or some combination of these features.

In still other variations on this process, the process may have a Delta BDO at least 18.68% higher than a process utilizing Ligand A1 catalyst instead of Ligand B2 catalyst, or a Delta MPDiol at least 16.51% lower than a process utilizing Ligand A1 catalyst instead of Ligand B2 catalyst, or some combination of these features.

In yet other variations, the process may further comprise adding DPB to the reactor. In some cases, this may include maintaining a DPB level of 100 ppm in the reactor.

In another embodiment, the presently disclosed technique is a process for producing HBA comprising reacting AA with CO/$H_2$ in a reactor in the presence of a catalyst system comprising rhodium complex and Ligand B2 having a BDO selectivity greater than 86.6% and preferably greater than 88.64%.

In still another embodiment, the presently disclosed technique is a process for producing HBA comprising reacting AA with CO/$H_2$ in a reactor in the presence of a catalyst system comprising rhodium complex and Ligand B2 having a BDO selectivity: MPDiol selectivity ratio greater than 7.19 and preferably greater than 8.54.

The following literature is hereby incorporated by reference for purposes as if set forth verbatim herein:

U.S. Pat. No. 4,215,077, entitled, "Hydroformylation of Olefins", issued Jul. 29, 1980, to Kuraray Co., Ltd. as assignee of the inventors Mitsuo Matsumoto and Masuhiko Tamura;

U.S. Pat. No. 4,567,305, entitled, "Process for Continuous Hydroformylation of Allyl Alcohol", issued Jan. 28, 1986, to Kuraray Company, Ltd. and Daicel Chemical Industries, Ltd. as assignees of the inventors Mitsuo Matsumoto, et al.

U.S. Pat. No. 6,225,509, entitled, "Allyl Alcohol Hydroformylation", issued May 1, 2001, to ARCO Chemical Technology, L.P. as assignee of the inventors Walter S. Dubner and Wilfred Po-sum Shum;

U.S. Pat. No. 7,271,295, entitled, "Hydroformylation Process", issued Sep. 18, 2007, to Lyondell Chemical Technology, L.P. as assignee of the inventors Daniel F, White and Walter S. Dubner;

U.S. Pat. No. 7,279,606, entitled, "Hydroformylation Process", issued Oct. 9, 2007, to Lyondell Chemical Technology, L.P. as assignee of the inventor Daniel F. White; and U.S. Pat. No. 7,294,602, entitled, "Hydroformylation Process", issued Nov. 13, 2007, to Lyondell Chemical Technology, L.P. as assignee of the inventor Daniel F. White.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A process for producing 4-hydroxybutyraldehyde comprising reacting allyl alcohol with CO/$H_2$ in a reactor in the presence of a catalyst system comprising rhodium complex and trans-1,2-bis[bis(3,5-di-n-alkylphenyl)phosphino]-cyclobutane at a pressure of about 50 psi or lower.

2. The process of claim 1, wherein the pressure is in the range of about 50 psi to about 35 psi.

3. The process of claim 1, further having a Butanediol selectivity greater than 86.6%.

4. The process of claim 1, further having a 2-Methylpropanediol selectivity lower than 12.05%.

5. The process of claim 1, further having a Butanediol selectivity: 2-Methylpropanediol selectivity ratio greater than 7.19.

6. The process of claim 1, further having a Butanediol equivalent yield greater than 98.65%.

7. The process of claim 1, having a Butanediol equivalent yield at least 0.42% higher than a process utilizing 2,3-O-isopropylidene-2,3-dihydroxy-1,4-bis[bis(3,5-di-n-alkylphenyl)phosphino]butane catalyst instead of trans-1,2-bis[bis(3,5-di-n-alkylphenyl)phosphino]-cyclobutane catalyst.

8. The process of claim 1, having a Delta Butanediol at least 18.68% higher than a process utilizing 2,3-O-isopropylidene-2,3-dihydroxy-1,4-bis[bis(3,5-di-n-alkylphenyl)phosphino] butane catalyst instead of trans-1,2-bis[bis(3,5-di-n-alkylphenyl)phosphino]-cyclobutane catalyst.

9. The process of claim 1, having a Delta 2-Methylpropanediol at least 16.51% lower than a process utilizing 2,3-O-isopropylidene-2,3-dihydroxy-1,4-bis[bis(3,5-di-n-alkylphenyl)phosphino]butane catalyst instead of trans-1,2-bis[bis(3,5-di-n-alkylphenyl)phosphino]-cyclobutane catalyst.

10. The process of claim 1, further comprising adding Diphenylphosphinobutane to the reactor.

11. The process of claim 10, wherein the step of adding Diphenylphosphinobutane to the reactor further comprises maintaining a Diphenylphosphinobutane level of 100 ppm in the reactor.

12. A process for producing 4-hydroxybutyraldehyde comprising reacting allyl alcohol with $CO/H_2$ in a reactor in the presence of a catalyst system comprising rhodium complex and trans-1,2-bis[bis(3,5-di-n-alkylphenyl)phosphino]-cyclobutane having a Butanediol selectivity greater than 86.6%.

13. A process for producing 4-hydroxybutyraldehyde comprising reacting allyl alcohol with $CO/H_2$ in a reactor in the presence of a catalyst system comprising rhodium complex and trans-1,2-bis[bis(3,5-di-n-alkylphenyl)phosphino]-cyclobutane having a Butanediol selectivity: 2-Methylpropanediol selectivity ratio greater than 7.19.

\* \* \* \* \*